United States Patent [19]

van de Werken

[11] Patent Number: Plant 7,534

[45] Date of Patent: May 28, 1991

[54] 'MINIKIN'

[75] Inventor: Hendrik van de Werken, Knoxville, Tenn.

[73] Assignee: The University of Tennessee Research Corporation, Knoxville, Tenn.

[21] Appl. No.: 271,919

[22] Filed: Nov. 16, 1988

[51] Int. Cl.[5] ..... A01H 5/00

[52] U.S. Cl. ..... Plt./54

[58] Field of Search ..... Plt./54

[56] References Cited

PUBLICATIONS van de Werken (1988), "Mutant Offspring", *American Nurseryman*, vol. 167, No. 1 (Jan. 1, 1988), pp. 127–132.

Fincham, J. R. S., "Ionizing Radiation", *Genetics*, Jones and Bartlett Pub. Inc., Boston, 1983, pp. 326–333.

Decourtye, L. (1978), "Utilisation de la Mutagenese pour l'Obtention de Nouvelles Varietes d'Arbustes Ornementaux", Comptes Rendus des Seances de l'Academie d'Agriculture de France, vol. 64 (8), pp. 664–669.

"Arnoldia," vol. 31, No. 2, The Arnold Arboretum, Mar. 1971, pp. 41–63.

"Flowering Shrubs," Zucker, Isabel, 1966, D. Van Nostrand Co., Inc., New York, N.Y., p. 380.

"Hilliers Manual of Trees & Shrubs," 2nd American Edition, Hilliers & Sons Ltd., 1979, A. S. Barnes & Co., Cranbury, N.J., p. 575.

"Hortus Third, A Concise Dictionary of Plants Cultivated in the United States and Canada," Staff of L. H. Bailey Hortorium, Cornell University, 1976, MacMillan Publishing Co., New York, N.Y., p. 1290.

"Manual of Woody Landscape Plants—Their Identification, Ornamental Characteristics, Propagation and Uses," Dirr, Michael A., 1983, Stipes Publishing Co., Champaign, Ill., p. 826.

*Primary Examiner*—James R. Feyrer

*Attorney, Agent, or Firm*—William H. Elliott, Jr.

[57] ABSTRACT

A new cultivar of Forsythia named 'Minikin' characterized by its small ultimate size, small narrow foliage, small flowers, slow and compact growth habit, excellent propagation from stem cuttings, hardiness, and its fine-textured overall appearance.

3 Drawing Sheets

This invention relates to a new variety of Forsythia cv. "Minikin", which is characterized especially by the small size of its leaves, flowers, stems, and internodes, and by its overall small stature.

The new variety was derived as a seedling from a vegetative line of mutants, which had been produced in turn by subjecting rooted cuttings of the parent *Forsythia intermedia* "Lynwood Gold" (a sport of *F. intermedia* "Spectabilis") to irradiation with 1,200 rad fast neutrons.

In 1968, three hundred cuttings of "Lynwood Gold" that had been potted and held in cold storage (38° F.) for six weeks and then returned to the greenhouse for two days were irradiated with 1200 rad fast neutrons. One of the plants of this group that broke dormancy formed a shoot with variegated foliage. This plant was cut back repeatedly to induce branching and eventually formed shoots that exhibited different characteristics. Each shoot was propagated by stem cuttings over 10 vegetative generations of selection and propagation. From this plant population two vegetatively selected types and three seedlings were selected. Further propagation and testing of these selections over several more years were shown to be the stable and new forsythia varieties that are the subject of this and four other copending plant patent applications; viz:

| Ser. No. | Name | Type |
|---|---|---|
| 272,063 | "Lemon-Screen" | vegetative selection |
| 273,489 | "Tinkle Bells" | vegetative selection |
| 271,919 | "Minikin" | seedling |
| 271,665 | "Fairy Land" | seedling |
| 271,666 | "Pygmy-Red" | seedling |

Each differs greatly from the parent "Lynwood Gold" and also from one another.

"Minikin" was selected at the seedling stage because of its small and linear foliage and short internodes. Stem cuttings from this plant have been rooted in soil and asexually propagated, and its progeny have displayed homogeneous and stable characteristics.

Throughout this specification, color names beginning with a small letter signify that the name of the color as used in common speech are aptly descriptive. Color names beginning with a capital letter designate values based on the R.H.S. Colour Chart, published by The Royal Horticultural Society of London, England.

The accompanying drawings illustrate the new variety in color as grown in Knox County within the State of Tennessee.

Figure 1:
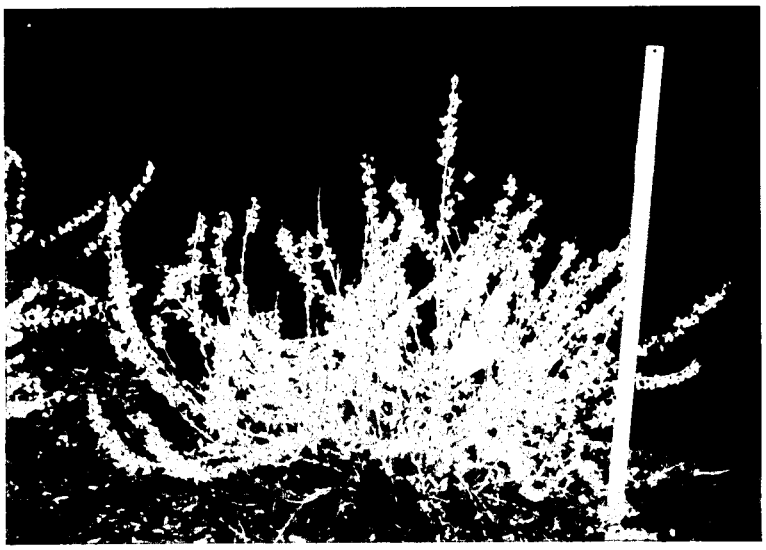
FIG. 1 illustrates "Minikin" as a 5½ year old plant in bloom in March.
Figure 2:
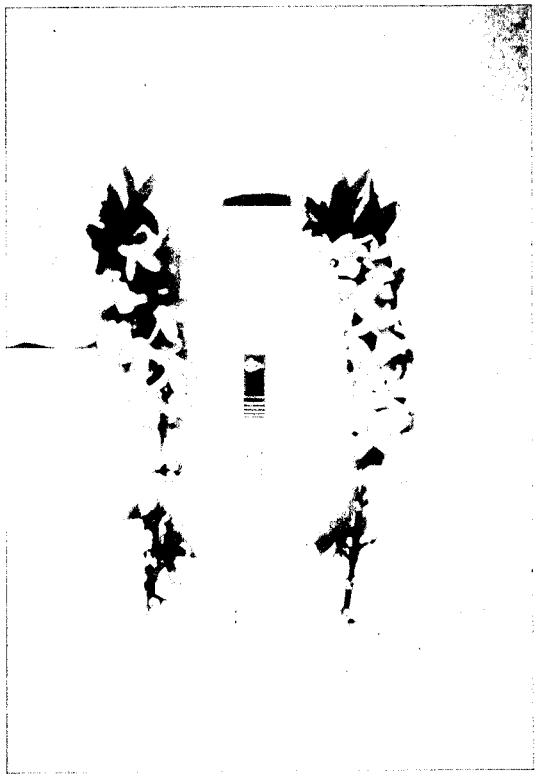
FIG. 2 shows flowered cut stems of "Minikin".
Figure 3:
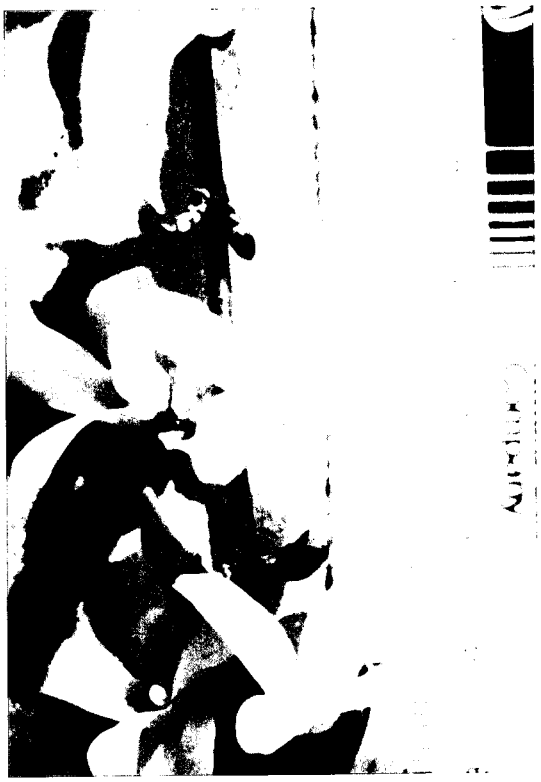
FIG. 3 is a close-up view of the flowers of FIG. 2.
Figure 4:
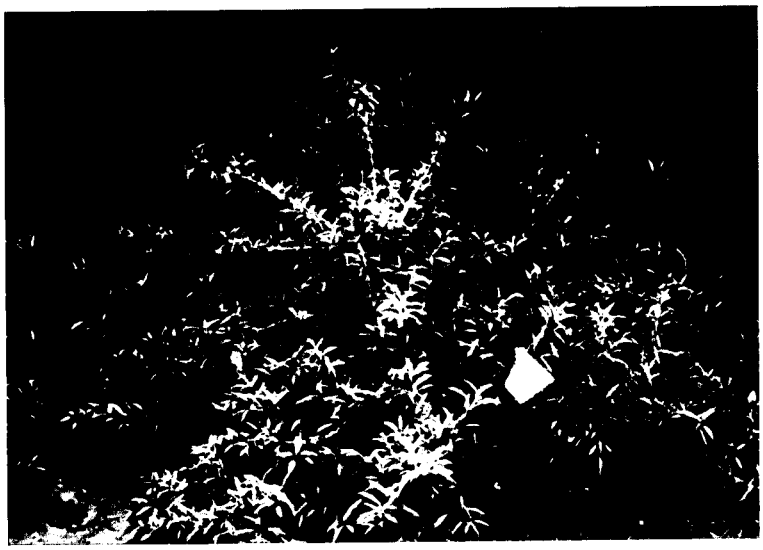
FIG. 4 illustrates the "Minikin" plant in full summer foliage. The white flag is 2.5 inches wide.
Figure 5:
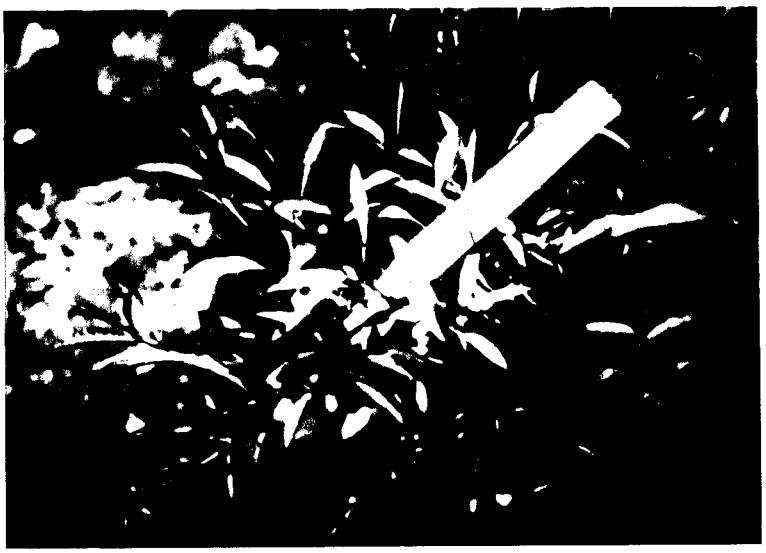
FIG. 5 is a closer view of the foliage shown in FIG. 4. The white label is 0.6 inch wide and 5 inches long.

The following characteristics distinguish "Minikin" from its parent and other Forsythia cultivars:

THE PLANT

"Minikin" is an attractive, fine textured, densely foliated cultivar, especially suited for container culture; ultimate size of "Minikin" is 2 ft. to 2½ ft. in height and 3 ft. to 4 ft. wide.

"Minikin" does not require the degree of winter protection required for most container grown genera. It is hardy in Zone 6b or lower. Because of its size and character, "Minikin" is suited for forcing into bloom before the normal flowering season and being sold as a potted floral plant which can be planted in a landscape later. The "Minikin" cultivar exhibits good vigor, but grows slowly. It requires no pruning to maintain its size and shape, except for cosmetic or rejuvenation purposes. It layers naturally and forms abundant seed pods. Its size and texture make it suitable for mass or ground cover use, or as a background plant for flower borders, as well as a specimen plant in a small garden or planter box.

Its parent, "Lynwood Gold", by contrast is tall and slender—a straight upright variety with erect stems and which attains a height of 6 ft. to 7½ ft. at maturity.

FLOWER

The flowers of "Minikin" are small (½" to ¾" in width) Yellow 9 A in color and there are two to four flowers per node. The "Minikin" flowers are fully reflexed (cup shaped), with four short, recurved petals. Corolla lobes are very small and strongly reflexed. The short pistils are 1/25 in. below the pollen sacs of the stamen. The flowering date is intermediate.

The "Lynwood Gold" parent is fertile and has pistils that extend well above its pollen sacs, is late flowering and its medium sized flowers (about 1" to 1½" in diameter) are almost evenly spaced on the stem. The flowers of "Lynwood Gold" are brilliant yellow (lighter than its parent, F. Spectabilis). The corolla lobes of "Lynwood Gold" are reflexed and its petals are large, broad open and elliptic.

SHOOTS

The "Minikin" internodes on flowering shoots are only ¼ in. to ¾ in. long; and on vegetative shoots the internodes are up to 2 inches long.

"Minikin" stems are light green when young and brownish green when mature. Stems are ascending and strongly lamellate between nodes.

The stems of the "Lynwood Gold" parent are green when young and brown when mature; they are a bit stiff; the pith at the nodes is lamellate, and on one year shoots, the stems between nodes are hollow.

FOLIAGE

The leaves of Minikin are simple, lightly serrate and linear, being acuminate at the tip and attenuate at the base. Young and mature leaves vary from bright green to dark green and in the fall a faded green until leaf drop. Venation is pinnate. The leaf blades on vegetative shoots are only about ¼ in. wide and 1½ inches long, attached to a ½ in. long slender petiole; the leaves on flowering shoots are smaller.

The leaves of the "Lynwood Gold" parent, on the other hand, are ovate lanceolate in shape and about 3" to 4½" long and about 1" to 1½" wide. Both young and old leaves are deep green in color.

To facilitate the comparison of the characteristics and features of "Minikin", the subject of this application, and its parent, "Lynwood Gold" and also with the four other new mutant offspring varieties of "Lynwood Gold" referred to above, there are attached hereto as Tables 1-5 comparative tabulations of the characteristics and properties of parent and its five offspring mutants that were developed from a single irradiated plant of "Lynwood Gold." Table 1 compares "Minikin" and its parent "Lynwood Gold". Table 2 compares "Minikin" and "Pygmy-Red". Table 3 compares "Minikin" and "Tinkle Bells". Table 4 compares "Minikin" and "Lemon-Screen". Table 5 compares "Minikin" and "Fairy Land".

TABLE 1

| Ser. No. 271,919 | |
|---|---|
| **MINIKIN** | |
| Plant: | |
| Habit | Small stature, fine textured; small leaves and small stems; densely foliated |
| Size, height | 2'-2½' |
| Size, width | 3'-4' |
| Vigor | Good vigor but slow growth |
| Hardiness | Zone 6b (or lower) |
| Productivity | Layers naturally Abundant seed pods |
| Stems or Shoots: | |
| Color (young) | Light green |
| Color (mature) | Brownish green |
| Rigidity | Ascending strongly lamellate between nodes |
| Leaves: | |
| Type | Simple |
| Color: | |
| (young) | Bright green to dark green |
| (mature) | Bright green to dark green |
| (fall) | Fading green until leaf drop |
| Shape | Linear |
| tip | Accuminate |
| base | Attenuate |
| margins | Lightly serrate |
| Size: | |
| length | On vegetative shoots-1½" attached to ½" long slender petiole; smaller on flowering shoots |
| width | On vegetative shoots - ¼"; |
| Venation | Pinnate |
| Flower: | |
| Date of Flowering | Intermediate |
| Size: width | ½"-¾" (cup shaped) fully reflexed |
| Color: | Yellow (9A) |
| Corolla: length | |
| lobes | strongly reflexed, very small |
| Petals: number | 4: - short and recurved |
| Pistils: | Short; 1/25" below pollen sacs of stamens |
| Number per node: | 2-4 |
| Insertion angle on upright stems: | |
| Internodes: | Short (Flowering shoots ¼-¾" Vegetative shoots up to 2") |
| Stress Resistance: | Doesn't require same degree of winter protection as most container grown plants of genre |
| Utility Aspects: | Blooming can be forced. Especially suited for container culture. |
| **LYNWOOD GOLD** | |
| Plant: | |
| Habit | Tall, slender-Upright straight & erect stems |
| Size, height | 6'-7½' |
| Size, width | |
| Vigor | |
| Hardiness | |
| Productivity | Fertile |
| Stems or Shoots: | |
| Color (young) | Green |
| Color (mature) | Brown |
| Rigidity | A bit stiff; pith nodes lamellate; hollow between nodes on one year shoots |
| Leaves: | |
| Type | |
| Color: | |
| (young) | Deep Green |
| (mature) | Deep Green |
| (fall) | |
| Shape | ovate lanceolate |
| tip | |
| base | |

TABLE 1-continued

| Ser. No. 271,919 | |
|---|---|
| margins | |
| Size: | |
| length | 3–4½" |
| width | 1–1½" |
| Venation | |
| Flower: | |
| Date of Flowering | Late |
| Size: width | 1"–1½" (medium) |
| Color: | Brillant Yellow (lighter than its parent Spectabilis) |
| Corolla: length | |
| lobes | Reflexed |
| Petals: number | Large, broad, open |
| | Elliptic |
| Pistils: | Extend well above pollen sacs (anthers) of stamens |
| Number per node: | |
| Insertion angle on upright stems: | |
| Internodes: | Flowers almost evenly spaced on stems |
| Stress Resistance: | |
| Utility Aspects: | |

TABLE 2

| | Ser. No. 271,919 MINIKIN |
|---|---|
| Plant: | |
| Habit | Small stature, fine textured; small leaves and small stems; densely foliated |
| Size, height | 2'–2½' |
| Size, width | 3'–4' |
| Vigor | Good vigor but slow growth |
| Hardiness | Zone 6b (or lower) |
| Productivity | Layers naturally Abundant seed pods |
| Stems or Shoots: | |
| Color (young) | Light green |
| Color (mature) | Brownish green |
| Rigidity | Ascending strongly lamellate between nodes |
| Leaves: | |
| Type | Simple |
| Color: | |
| (young) | Bright green to dark green |
| (mature) | Bright green to dark green |
| (fall) | Fading green until leaf drop |
| Shape | Linear |
| tip | Accuminate |
| base | Attenuate |
| margins | Lightly serrate |
| Size: | |
| length | On vegetative shoots-1½" attached to ½" long slender petiole; smaller on flowering shoots |
| width | On vegetative shoots - ¼"; |
| Venation | Pinnate |
| Flower: | |
| Date of Flowering | Intermediate |
| Size: width | ½"–¾" (cup shaped) fully reflexed |
| Color: | Yellow (9A) |
| Corolla: length | |
| lobes | strongly reflexed, very small |
| Petals: number | 4: - short and recurved |
| Pistils: | Short; 1/25" below pollen sacs of stamens |
| Number per node: | 2–4 |
| Insertion angle on upright stems: | |
| Internodes: | Short (Flowering shoots ½–¾" Vegetative shoots up to 2") |
| Stress Resistance: | Doesn't require same degree of winter protection as most container grown plants of genre |
| Utility Aspects: | Blooming can be forced. Especially suited for container culture. |

TABLE 2-continued

| | Ser. No. 271,666 PYGMY RED |
|---|---|
| Plant: | |
| Habit | Low, loose graceful arching to ground |
| Size, height | 3½'–4½' |
| Size, width | 5'–6' |
| Vigor | Good vigor |
| Hardiness | Hardy Zone 6b (or lower) |
| Productivity | Readily roots where branches touch ground few seed pods |
| Stems or Shoots: | |
| Color (young) | High anthocyanin |
| Color (mature) | Purple Red (59A) |
| Rigidity | Flexible lamellate between nodes |
| Leaves: | |
| Type | Simple |
| Color: | |
| (young) | Dark Green |
| (mature) | Dark Green |
| (fall) | Anthocyanin (maroon) expressed in full sun |
| Shape | Lanceolate (few lobed leaves on vegetative shoots) |
| tip | Accuminate |
| base | Attenuate |
| margins | Serrate |
| Size: | |
| length | 2"–2½" on flowering wood; to 2¾" on vegatative wood |
| width | 0.3"–0.4" on flowering wood; to 1" on vegetative wood |
| Venation | Pinnate |
| Flower: | |
| Date of Flowering | Intermediate |
| Size: width | 1¼"–1½" |
| Color: | Yellow (7A) |
| Corolla: length | |
| lobes | Narrow |
| Petals: number | 4 - sometimes 5 |
| Pistils: | Extend 2/25"–3/25" above pollen sacs of stamens |
| Number per node: | 2 |
| Insertion angle on upright stems: | |
| Internodes: | 1"–1½" (1½" even on fast growning shoots) |
| Stress Resistance: | disease and insect |
| Utility Aspects: | |

TABLE 3

| | Ser. No. 271,919 MINIKIN |
|---|---|
| Plant: | |
| Habit | Small stature, fine textured; small leaves and small stems; densely foliated |
| Size, height | 2'–2½' |
| Size, width | 3'–4' |
| Vigor | Good vigor but slow growth |
| Hardiness | Zone 6b (or lower) |
| Productivity | Layers naturally Abundant seed pods |
| Stems or Shoots: | |
| Color (young) | Light green |
| Color (mature) | Brownish green |
| Rigidity | Ascending strongly lamellate between nodes |
| Leaves: | |
| Type | Simple |
| Color: | |
| (young) | Bright green to dark green |
| (mature) | Bright green to dark green |
| (fall) | Fading green until leaf drop |
| Shape | Linear |
| tip | Accuminate |
| base | Attenuate |

TABLE 3-continued

| | |
|---|---|
| margins | Lightly serrate |
| Size: | |
| length | On vegetative shoots-1½" attached to ½" long slender petiole; smaller on flowering shoots |
| width | On vegetative shoots - ¼"; |
| Venation | Pinnate |
| Flower: | |
| Date of Flowering | Intermediate |
| Size: width | ½"-¾" (cup shaped) fully reflexed |
| Color: | Yellow (9A) |
| Corolla: length | |
| lobes | strongly reflexed, very small |
| Petals: number | 4: - short and recurved |
| Pistils: | Short; 1/25" below pollen sacs of stamens |
| Number per node: | 2–4 |
| Insertion angle on upright stems: | |
| Internodes: | Short (Flowering shoots ¼-¾" Vegetative shoots up to 2") |
| Stress Resistance: | Doesn't require same degree of winter protection as most container grown plants of genre |
| Utility Aspects: | Blooming can be forced. Especially suited for container culture. |

Ser. No. 273,489
TINKLE BELLS

| | |
|---|---|
| Plant: | |
| Habit | Semi-dwarf: Upright |
| Size, height | 4'-4½' |
| Size, width | |
| Vigor | Medium vigor |
| Hardiness | Hardy Zone 6b (or lower) |
| Productivity | Does not layer naturally (replicates from stools (no seed pods observed) |
| Stems or Shoots: | |
| Color (young) | Yellow Green |
| Color (mature) | Light brown |
| Rigidity | Sparsely lamellate between nodes - Rigid |
| Leaves: | |
| Type | Simple |
| Color: | |
| (young) | Medium Green |
| (mature) | Medium Green |
| (fall) | Faded green to yellow |
| Shape | Elliptical |
| tip | Acute on flower shoots accuminate on vegetative shoots |
| base | |
| margins | serrate on upper ⅓ near tip |
| Size: | |
| length | 2"-3" (with petiole) |
| width | ½" |
| Venation | Pinnate |
| Flower: | |
| Date of Flowering | Early |
| Size: width | ½"-¾" at 45° angle |
| Color: | Bright Yellow (7B) |
| Corolla: length | ½" open to 45° angle |
| lobes | not reflexed during prime |
| Petals: number | 4; occasionally 5 or 6 |
| Pistils: | short: anthers slightly below stigma portion of pistil |
| Number per node: | 2; often 4 per node |
| Insertion angle on upright stems: | buds & flowers pendulous |
| Internodes: | ½"-1½" |
| Stress Resistance: | Disease and insect |
| Utility Aspects: | Can force flowering suitable for container culture |

TABLE 4

Ser. No. 271,919
MINIKIN

TABLE 4-continued

| | |
|---|---|
| Plant: | |
| Habit | Small stature, fine textured; small leaves and small stems; densely foliated |
| Size, height | 2'-2½' |
| Size, width | 3'-4' |
| Vigor | Good vigor but slow growth |
| Hardiness | Zone 6b (or lower) |
| Productivity | Layers naturally Abundant seed pods |
| Stems or Shoots: | - |
| Color (young) | Light green |
| Color (mature) | Brownish green |
| Rigidity | Ascending strongly lamellate between nodes |
| Leaves: | |
| Type | Simple |
| Color: | |
| (young) | Bright green to dark green |
| (mature) | Bright green to dark green |
| (fall) | Fading green until leaf drop |
| Shape | Linear |
| tip | Accuminate |
| base | Attenuate |
| margins | Lightly serrate |
| Size: | |
| length | On vegetative shoots-1½" attached to ½" long slender petiole: smaller on flowering shoots |
| width | On vegetative shoots - ¼"; |
| Venation | Pinnate |
| Flower: | |
| Date of Flowering | Intermediate |
| Size: width | ½"-¾" (cup shaped) fully reflexed |
| Color: | Yellow (9A) |
| Corolla: length | |
| lobes | strongly reflexed, very small |
| Petals: number | 4: - short and recurved |
| Pistils: | Short; 1/25" below pollen sacs of stamens |
| Number per node: | 2–4 |
| Insertion angle on upright stems: | |
| Internodes: | Short (Flowering shoots ¼-¾" Vegetative shoots up to 2") |
| Stress Resistance: | Doesn't require same degree of winter protection as most container grown plants of genre |
| Utility Aspects: | Blooming can be forced. Especially suited for container culture. |

Ser. No. 272,063
LEMON SCREEN

| | |
|---|---|
| Plant: | |
| Habit | Tall, open and graceful; Upright, fan shape; vigorous; open foliage |
| Size, height | Up to 10' |
| Size, width | Hardy Zone 6b (or lower) |
| Vigor | Vigorous |
| Hardiness | |
| Productivity | Abundant Flowers/highly sterile/ pruned wood branches quickly |
| Stems or Shoots: | |
| Color (young) | |
| Color (mature) | Yellow |
| Rigidity | Slightly lamellate between nodes |
| Leaves: | |
| Type | Simple |
| Color: | |
| (young) | Yellow green 151 B or Chartreuse (appear after flowering) |
| (mature) | Normal green (Yellow-Green 144) whitish blotches |
| (fall) | Greyed Purple 187 B |
| Shape | |
| tip | Accuminate |
| base | Attenuate |
| margins | Serrate |

TABLE 4-continued

| | |
|---|---|
| Size: | |
| length | Not distinguishing |
| width | Not distinguishing |
| Venation | Pinnate |
| Flower: | |
| Date of Flowering | Early |
| Size: width | 1½"-1¾" |
| Color: | Yellow (6C) |
| Corolla: length | |
| lobes | Somewhat reflexed |
| Petals: number | 4, sometimes fasciated |
| Pistils: | aborted stamens &/or pistils |
| Number per node: | 4 to 8 |
| Insertion angle on upright stems: | |
| Internodes: | 1" to 2" long on flowering wood |
| Stress Resistance: | Summer foliage disease & insect resistant |
| Utility Aspects: | Summer pruning leads to shoot with chartreuse leaves (young) |

TABLE 5

| | Ser. No. 271,919 MINIKIN |
|---|---|
| Plant: | |
| Habit | Small stature, fine textured; small leaves and small stems; densely foliated |
| Size, height | ½'-2½' |
| Size, width | 3'-4' |
| Vigor | Good vigor but slow growth |
| Hardiness | Zone 6b (or lower) |
| Productivity | Layers naturally<br>Abundant seed pods |
| Stems or Shoots: | |
| Color (young) | Light green |
| Color (mature) | Brownish green |
| Rigidity | Ascending strongly<br>lamellate between nodes |
| Leaves: | |
| Type | Simple |
| Color: | |
| (young) | Bright green to dark green |
| (mature) | Bright green to dark green |
| (fall) | Fading green until leaf drop |
| Shape | Linear |
| tip | Accuminate |
| base | Attenuate |
| margins | Lightly serrate |
| Size: | |
| length | On vegetative shoots-1½" attached to ½" long slender petiole; smaller on flowering shoots |
| width | On vegetative shoots - ¼"; |
| Venation | Pinnate |
| Flower: | |
| Date of Flowering | Intermediate |
| Size: width | ½"-¾" (cup shaped) fully reflexed |
| Color: | Yellow (9A) |
| Corolla: length | |
| lobes | strongly reflexed, very small |
| Petals: number | 4: - short and recurved |
| Pistils: | Short; 1/25" below pollen sacs of stamens |
| Number per node: | 2-4 |
| Insertion angle on upright stems: | |
| Internodes: | Short (Flowering shoots ¼-¾" Vegetative shoots up to 2") |
| Stress Resistance: | Doesn't require same degree of winter protection as most container grown plants of genre |
| Utility Aspects: | Blooming can be forced. Especially suited for container culture. |

TABLE 5-continued

| | Ser. No. 271,665 FAIRY LAND |
|---|---|
| Plant: | |
| Habit | Small overall & fine textured:<br>Closely spaced flowers & leaves<br>Dense (young) foliage |
| Size, height | 3'-4' |
| Size, width | 5'-6' |
| Vigor | Good vigor for size |
| Hardiness | Zone 6b (or lower) |
| Productivity | Few seed pods |
| Stems or Shoots: | |
| Color (young) | Light green |
| Color (mature) | Brownish green |
| Rigidity | Very flexible lamellate between nodes |
| Leaves: | |
| Type | Simple |
| Color: | |
| (young) | Medium green (fairly light) |
| (mature) | Medium green (fairly light) |
| (fall) | Mostly faded yellow |
| Shape | Lanceolate |
| tip | Accuminate |
| base | Attenuate |
| margins | On flowering wood: entire<br>On vegetative wood: serrate top ⅓ |
| Size: | |
| length | On flowering wood: 1½"-2½"<br>On vegatative shoots: about 3" |
| width | On flowering wood: 0.2"-0.4"<br>On vegatative shoots 0.5-0.6" |
| Venation | Pinnate |
| Flower: | |
| Date of Flowering | Intermediate |
| Size: width | ¾"-1¼" |
| Color: | Yellow (6A) |
| Corolla: length | |
| lobes | Reflexed, small |
| Petals: number | Generally 4-many have 5, 6, 7 and 8 on single corolla |
| Pistils: | Extend 3/25" to 4/25" above pollen sacs (anthers) of the stamen |
| Number per node: | 2-4 |
| Insertion angle on upright stems: | |
| Internodes: | ¼" to about 1" |
| Stress Resistance: | |
| Utility Aspects: | Very well suited for container culture |

What is claimed is:

1. A new and distinct cultivar of Forsythia named 'Minikin', substantially as shown and described herein.

* * * * *